(12) United States Patent
Davydov (10) Patent No.: US 11,416,822 B2
(45) Date of Patent: Aug. 16, 2022

(54) MEDICAL BENEFIT MANAGEMENT SYSTEM AND METHOD

(71) Applicant: Zero Copay Program, Inc., New Hyde Park, NY (US)

(72) Inventor: Yuriy Davydov, Old Brookville, NY (US)

(73) Assignee: Zero Copay Program, Inc., New Hyde Park, NY (US)

( * ) Notice: Subject to any disclaimer, the term of this patent is extended or adjusted under 35 U.S.C. 154(b) by 263 days.

(21) Appl. No.: 16/448,481

(22) Filed: Jun. 21, 2019

(65) Prior Publication Data
US 2020/0402017 A1 Dec. 24, 2020

(51) Int. Cl.
*G16H 10/60* (2018.01)
*G06Q 10/10* (2012.01)

(52) U.S. Cl.
CPC ......... *G06Q 10/1057* (2013.01); *G16H 10/60* (2018.01)

(58) Field of Classification Search
CPC ........................... G06Q 10/1057; G16H 10/60
USPC ......................................................... 705/2–3
See application file for complete search history.

(56) References Cited

U.S. PATENT DOCUMENTS

| | | |
|---|---|---|
| 7,438,218 B2 | 10/2008 | Dooley et al. |
| 7,657,437 B2 | 2/2010 | Kalies |
| 7,912,741 B1 | 3/2011 | Pinsonneault |
| 8,060,379 B1 | 11/2011 | Pinsonneault et al. |
| 8,099,295 B2 | 1/2012 | Virdee et al. |
| 8,160,897 B1 * | 4/2012 | Lash ............... G06Q 10/10 705/2 |
| 8,452,608 B2 | 5/2013 | Smeeding et al. |
| 8,489,415 B1 | 7/2013 | Ringold |
| 8,515,784 B2 | 8/2013 | Russell |
| 8,577,691 B2 | 11/2013 | Hudson et al. |
| 8,635,083 B1 | 1/2014 | Casu |

(Continued)

FOREIGN PATENT DOCUMENTS

| | | |
|---|---|---|
| WO | 2013/082177 A1 | 6/2013 |
| WO | 2015/123540 A1 | 8/2015 |
| WO | 2018/049330 A1 | 3/2018 |

OTHER PUBLICATIONS

Yuriy Davydov; U.S. Appl. No. 16/448,559 filed Jun. 21, 2019.

*Primary Examiner* — Michael Tomaszewski
(74) *Attorney, Agent, or Firm* — Barclay Damon LLP (57) ABSTRACT

Medical benefit management systems and methods are disclosed herein. The system, in an embodiment, includes one or more data storage devices storing a plurality of instructions configured to be executed to perform a plurality of steps. The steps include receiving a provisioning request comprising a benefit specification from a first processor controlled by a product related entity; configuring a benefit processing business logic of the benefit processing system with the provisioning request; receiving a benefit submission from a second processor controlled by a dispensary entity or medical merchant; processing the benefit submission using the benefit processing business logic based on the benefit specification; generating a benefit transaction record related to the benefit submission; and displaying a first access interface to the product related entity and a second access interface to the dispensing entity, having different views to different portions of the benefit transaction record.

14 Claims, 8 Drawing Sheets

(56) References Cited

U.S. PATENT DOCUMENTS

| | | | |
|---|---|---|---|
| 8,639,523 | B1 | 1/2014 | Pinsonneault |
| 8,781,851 | B2 | 7/2014 | Anderson et al. |
| 8,788,293 | B2 | 7/2014 | Kennedy et al. |
| 10,475,140 | B2* | 11/2019 | Patel ................. G16H 15/00 |
| 2003/0055687 | A1* | 3/2003 | Rudy ................. G16H 40/20 |
| | | | 705/2 |
| 2003/0130868 | A1 | 7/2003 | Coelho |
| 2003/0149594 | A1 | 8/2003 | Beazley et al. |
| 2004/0073457 | A1 | 4/2004 | Kalies |
| 2004/0249745 | A1 | 12/2004 | Van Baaren |
| 2005/0010446 | A1* | 1/2005 | Lash ................. G06Q 40/08 |
| | | | 705/2 |
| 2005/0203828 | A1 | 9/2005 | Lyakovetsky |
| 2006/0149784 | A1 | 7/2006 | Tholl et al. |
| 2006/0212318 | A1 | 9/2006 | Dooley et al. |
| 2006/0247968 | A1* | 11/2006 | Kadry ............. G06Q 30/0255 |
| | | | 705/2 |
| 2007/0136100 | A1 | 6/2007 | Daugherty et al. |
| 2009/0055225 | A1 | 2/2009 | Russell |
| 2011/0257992 | A1 | 10/2011 | Scantland et al. |
| 2011/0313785 | A1* | 12/2011 | Lash ................. G06Q 40/00 |
| | | | 705/2 |
| 2012/0109839 | A1 | 5/2012 | Anderson et al. |
| 2012/0253833 | A1 | 10/2012 | John et al. |
| 2012/0303379 | A1* | 11/2012 | Lash ................. G06Q 40/00 |
| | | | 705/2 |
| 2013/0138453 | A1 | 5/2013 | Kuhn |
| 2013/0218595 | A1 | 8/2013 | Burkett |
| 2013/0253952 | A1* | 9/2013 | Burke ................ G16H 40/20 |
| | | | 705/3 |
| 2013/0275196 | A1 | 10/2013 | Smeeding et al. |
| 2014/0214435 | A1 | 7/2014 | Previdi |
| 2014/0244284 | A1 | 8/2014 | Sidney |
| 2015/0088532 | A1 | 3/2015 | McKinney et al. |
| 2015/0088552 | A1 | 3/2015 | McKinney et al. |
| 2015/0149197 | A1 | 5/2015 | Guinan |
| 2015/0254428 | A1 | 9/2015 | Burkett |
| 2015/0269695 | A1 | 9/2015 | Pinsonneault et al. |
| 2015/0278472 | A1 | 10/2015 | King et al. |
| 2015/0371338 | A1 | 12/2015 | Herman |
| 2016/0140593 | A1 | 5/2016 | Smeeding et al. |
| 2017/0344724 | A1 | 11/2017 | Nockley |
| 2018/0096105 | A1 | 4/2018 | Bleicher et al. |

* cited by examiner

MEDICAL BENEFIT MANAGEMENT SYSTEM AND METHOD

BACKGROUND

Conventional benefit management systems typically are based on monolithic software that incorporates business logic, database management, configuration, and administration in a system having a single administrative domain of access. In such systems, operators, typically employed by a single entity, control the system to make modifications, run reports, and add services and features. In some cases, these systems are run by companies that operate the system for one or more clients, such as medical product manufacturers.

The typical workflow in these conventional systems requires substantial human intervention to fulfill work orders or prepare reports for the various business entities that are involved in the operation of the system. For example, the on-ramping process for a new manufacturer might require prolonged discussions about how that manufacturer's business logic should interact with benefits and orders placed in the system, leading to the design and implementation of such logic, often in the form of configuration files. These files are then loaded into the system during a maintenance window or during another specified time of day with the goal of beginning operation in a future time period.

In another example, the operator prepares periodic reports for the various manufacturers by running database reporting software local to the systems. The operator then sends these reports to the different manufacturers for review. Any additional reports are conventionally filled by work orders taken by the operators of the benefit management system, and then manually forwarded to the requesting manufacturer.

In a further example, before loading of new benefits programs, it is conventionally necessary for the operator of the benefit management system to work with the manufacturer sponsoring the new benefits programs to design the business logic, and then reconfigure the system, typically during a maintenance window.

Many of the steps described above are disjointed, resulting in multiple stop-and-go points. In many cases, action is suspended at these points until acts are taken by certain users. Therefore, these points can cause delays, errors, complexity and inefficiencies in benefit management operations.

SUMMARY

In one embodiment, presented herein is a medical benefit management system related to medical benefit offerings. The system includes one or more data storage devices storing a plurality of instructions configured to be executed to perform the following. Receive a provisioning request from a first processor controlled by a product related entity, the provisioning request comprising a benefit specification. Configure a benefit processing business logic of the benefit processing system with the benefit specification. Receive a benefit submission from a second processor controlled by a dispensary entity. The benefit submission relates to the product benefit offering from the product related entity. Process the benefit submission using the benefit processing business logic based on the benefit submission. Generate a benefit transaction record related to the benefit submission. Display a first access interface to the product related entity and a second access interface to the dispensing entity. The first and second administrative interfaces are accessible during continued execution and comprise different views to different portions of the benefit transaction record related to the benefit submission.

In another embodiment, a method includes the following. Receiving a provisioning request from a first processor controlled by a product related entity. The provisioning request comprising a benefit specification. Configuring a benefit processing business logic of the benefit processing system with the provisioning request. Receiving a benefit submission from a second processor controlled by a dispensary entity. The benefit submission relates to the benefit specification from the product related entity. Processing the benefit submission using the benefit processing business based on the benefit submission. Generating a benefit transaction record related to the benefit submission. Displaying a first access interface to the product related entity and a second access interface to the dispensing entity. The first and second administrative interfaces are accessible during continued execution and comprise different views to different portions of the benefit transaction record related to the benefit submission.

In another embodiment, a benefit management system includes one or more data storage devices comprising a plurality of computer-readable instructions, and the instructions comprise a plurality of benefit business rules. One or more processors are operatively coupled to the one or more data storage devices. The one or more processors are configured to execute the instructions to perform the following. Receive offering data from the provider, where the offering data specifies one of a plurality of types of medical benefit offerings of a provider. Receive at least one rule customization input from the provider. Customize at least one of the benefit business rules based, at least in part, on the at least one rule customization input. Receive a benefit submission from a medical merchant, where the benefit submission is based, at least in part, on a medical request received by the medical merchant, where the medical request is provided by a customer. Process the benefit submission using the at least one customized business rule. Generate benefit transaction information related to the benefit submission, where the benefit transaction information comprises a first portion and a second portion that differs from the first portion. Cause a plurality of display devices to simultaneously display a provider interface accessible by the provider and a merchant interface accessible by the medical merchant Generate a benefit outcome based on the processing of the benefit submission, where the benefit outcome results in a benefit provided by the medical merchant to the healthcare customer.

The above embodiments are exemplary only. Other embodiments are within the scope of the disclosed subject matter.

BRIEF DESCRIPTION OF THE DRAWINGS

So that the manner in which the features of the disclosure can be understood, a detailed description may be had by reference to certain embodiments, some of which are illustrated in the accompanying drawings. It is to be noted, however, that the drawings illustrate only certain embodiments and are therefore not to be considered limiting of its scope, for the scope of the disclosed subject matter encompasses other embodiments as well. The drawings are not necessarily to scale, emphasis generally being placed upon illustrating the features of certain embodiments. In the drawings, like numerals are used to indicate like parts throughout the various views.

Corresponding reference characters indicate corresponding parts throughout several views. The examples set out herein illustrate several embodiments, but should not be construed as limiting in scope in any manner.

DETAILED DESCRIPTION

The present disclosure relates to systems for managing and processing benefit payments, and more particularly to a benefit management system and method with automated provisioning/configuration and real-time access. In an embodiment, the medical benefit management system is usable by product related entities or manufacturers. At the same time, the medical benefit management system is usable by medical merchants who sell, resell, gift or otherwise provide the manufacturers' products to customers. The customers can include recipients, patients and agents acting on behalf of patients or people in need of medical products. By way of overview, these techniques represent practical applications that advance the field of benefit management, by increasing the efficiency of provisioning and handling of medical benefit submissions. As one advantage, because the system continues to operate to handle benefit submissions and allow client or manufacturer interface access during provisioning of new business logic, users of the system can make real-time changes or additions to medical benefit offerings related to products that are immediately reflected. Depending on the embodiment, the medical benefit offerings can include coupons, discounts, rebates (instant or post-sale), freebies or other financial or monetary consideration.

Depending on the embodiment, a medical merchant can be a dispensary entity, pharmacy, medical clinic, medical equipment retailer, medical product dispensing company, retailer, store or other entity capable of selling, reselling, gifting or otherwise supplying medical products to customers. Depending on the transaction, the products may be goods or services that are manufactured, distributed, supplied, performed, rendered or marketed by the manufacturer. In some examples, a benefit offering may relate to a product that is or includes a physical item or good, such as a pharmaceutical product, drug, medical equipment, wheelchair, glucose meter, etc. In other examples, a benefit offering may relate to a product that is or includes a service or activity, such as a healthcare service, a home health visit service, a physical therapy session, etc. It should be understood that, if the product is or includes a service, the manufacturer of such product would be the conductor or performer of such product.

In addition, real-time interface access, segmented by the accessing user (e.g., medical merchant, dispensary or product related entities), allows for different entities to gain different views into the same data, depending upon their role in the business logic and affiliated relationships. In a similar manner, an entity may be blocked from viewing certain details of the data, if inconsistent with that entity's role. One example of this would be that a manufacturer may be deemed allowed to view the quantity of prescriptions filled, but payments by an insurance company may not be shown.

Figure 1A:
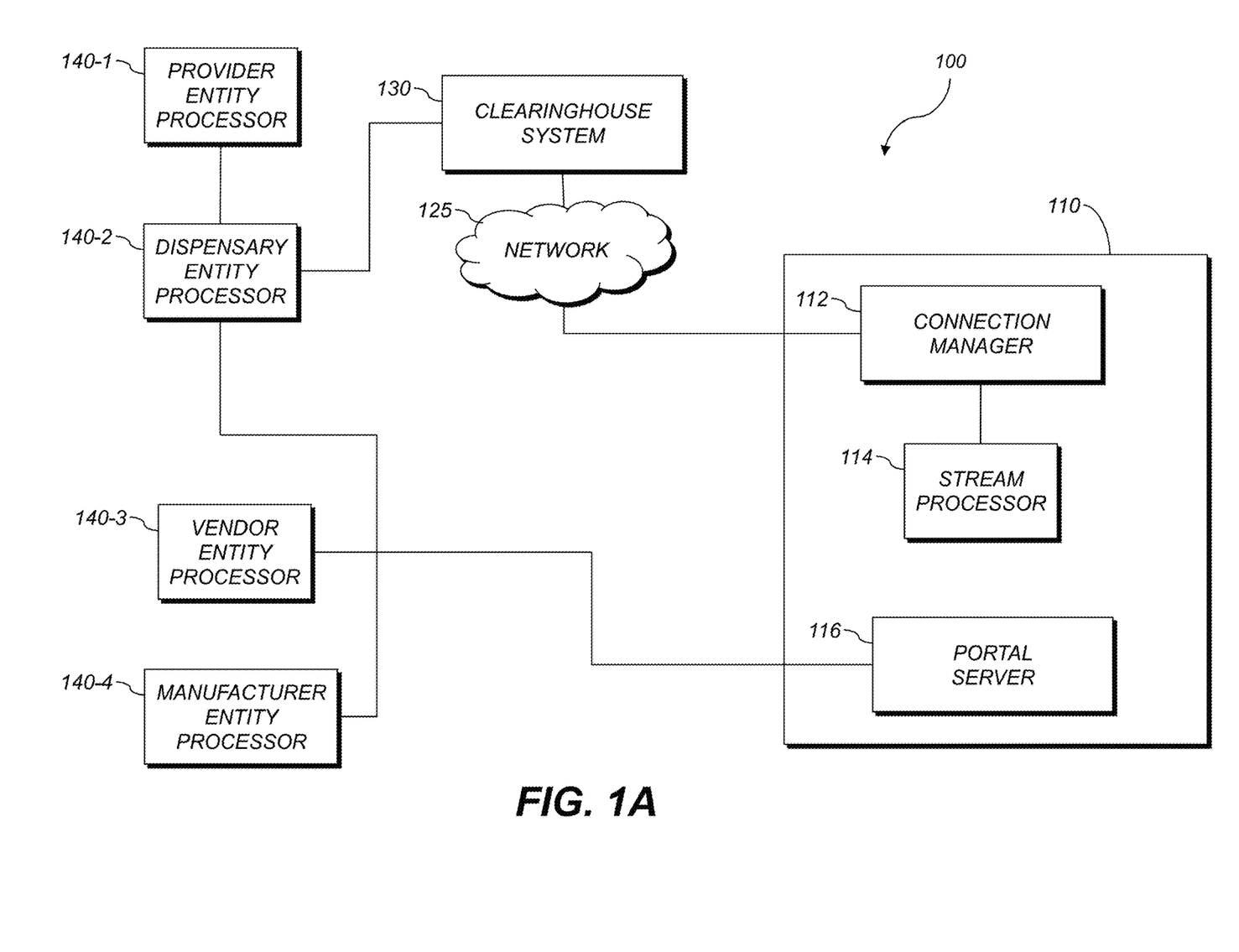
FIG. 1A is a block diagram of a benefit management system interoperating with other components or systems, in accordance with one or more aspects set forth herein.

FIG. 1A is a block diagram of a benefit management system 110, interoperating with other components. In the embodiment of FIG. 1A, the medical benefit management system 110 includes a connection manager 112, a stream processor 114, and interface or portal server 116. For example, the connection manager 112, the stream processor 114, and the interface server 116 may execute on one or more processors, on one or more computer systems, depending on the capacity required of the system.

For instance, the connection manager 112 is responsible for conducting networking communications with various entities connected to the medical benefit management system 110 via a network 125. These entities include a clearinghouse 130, and processors of different entities, such as a provider entity processor 140-1, a dispensary entity processor 140-2, a vendor entity processor 140-3, or a manufacturer entity processor 140-4. Different consumers, or patients, typical work with providers, such as doctors or the like, to receive a prescription or other indication for a need for a product to be procured from a dispensary. Vendors and manufacturers are examples of product related entities who are involved in supplying a benefit for a product. Examples of product related entities include drug manufacturers, representatives or vendors of drug, medical equipment, home health care visit, and the like, non-profit organizations for facilitating lower patient costs, insurance companies, etc. In short, product related entities can include any entity that is involved in the supply chain of a product.

There may be multiple of these entities managed in the operation of the medical benefit management system 110. For example, the medical benefit management system 110 may support multiple dispensaries, such as pharmacies, medical drug dispensaries, medical equipment suppliers, or any other place where products that are potential the subject of a benefit are sold or supplied to consumers. Similarly, the medical benefit management system 110 may be support multiple product related entities that are involved in the provisioning of a benefit related to a product. As another example, a single clearinghouse or multiple clearinghouses may be used to allow the medical benefit management system 110 to receive claims submissions from multiple dispensaries.

In addition, the medical benefit management system 110 includes a stream processor 114 for scalable management of streams of data sent and received from the medical benefit management system 110 to and from the various entities. In one implementation, Apache Kafka, provided by the Apache Software Foundation of Maryland, USA, may be used as a stream processor.

Further, the medical benefit management system 110 includes an interface server 116, which can allow different views of the data to be presented to different entities, each of which may log into the interface server 116 with appropriate credentials. In one implementation, Apache Server, provided by the Apache Software Foundation of Maryland, USA, may be used as an interface server 116.

The components depicted in FIG. 1A may communicate via one or more networks 125. The network 125 may be a public or private network, such as any network based on the Internet Protocol, or any similar protocol.

Figure 1B:
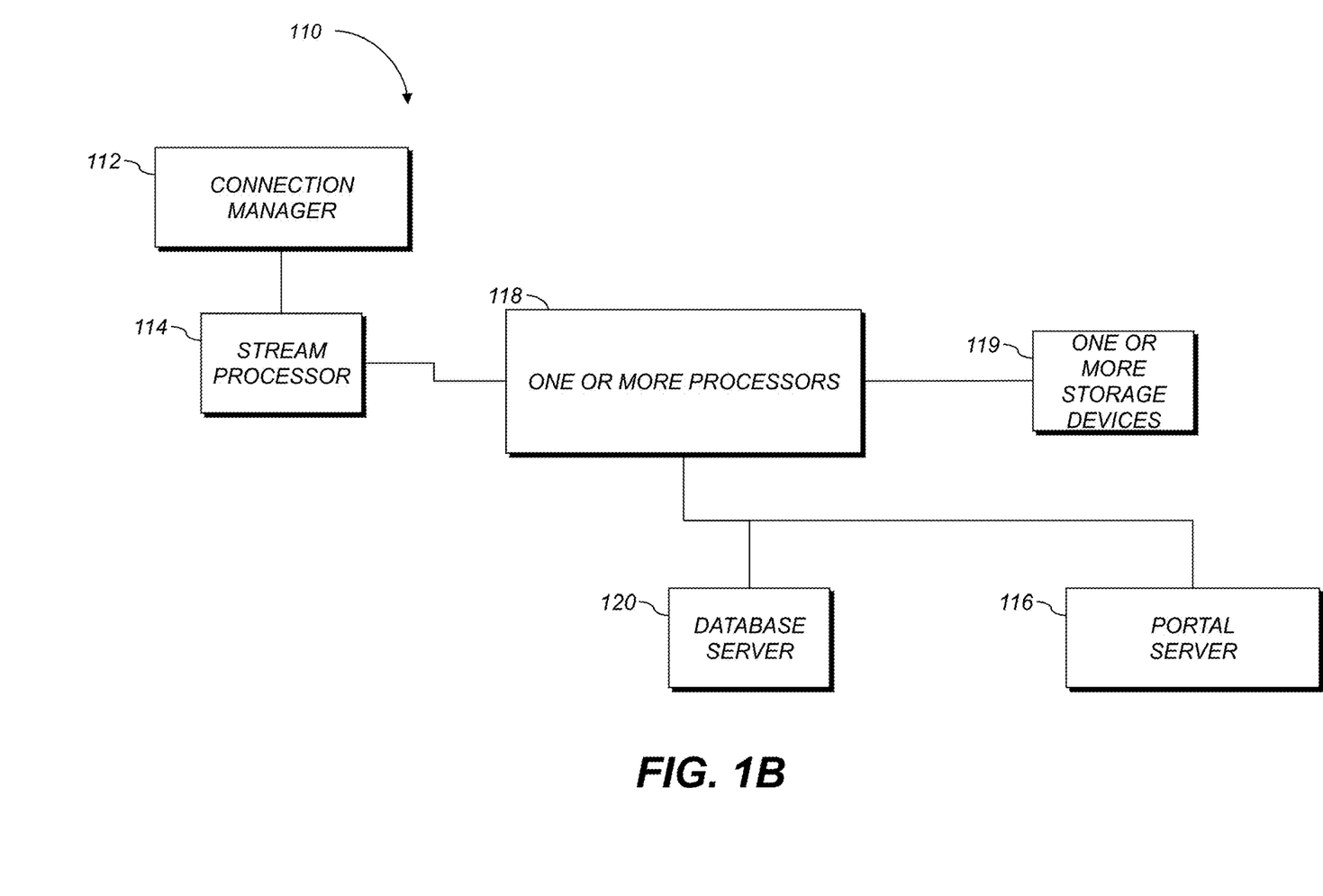
FIG. 1B is a block diagram depicting further details of a benefit management system, in accordance with one or more aspects set forth herein.

FIG. 1B is a block diagram depicting further details of a benefit management system 110. Further implementation details of the medical benefit management system 110, in the embodiment of FIG. 1B, include one or more processors 118, one or more storage devices 119 and a database server 120. For example, the one or more processors 118 may be used to execute a plurality of program instructions stored on the one or more storage devices 119. In addition, the database server 120 may be used to store the provisioning requests, claim submissions, business logic, processed claims, configuration files, etc., as described below. In one implementation, the database server 120 may be a PostgreSQL database, available as an open source software from The PostgreSQL Global Development Group. In other implementation, any database, such as an SQL or object oriented database, may be used.

Figure 2A:
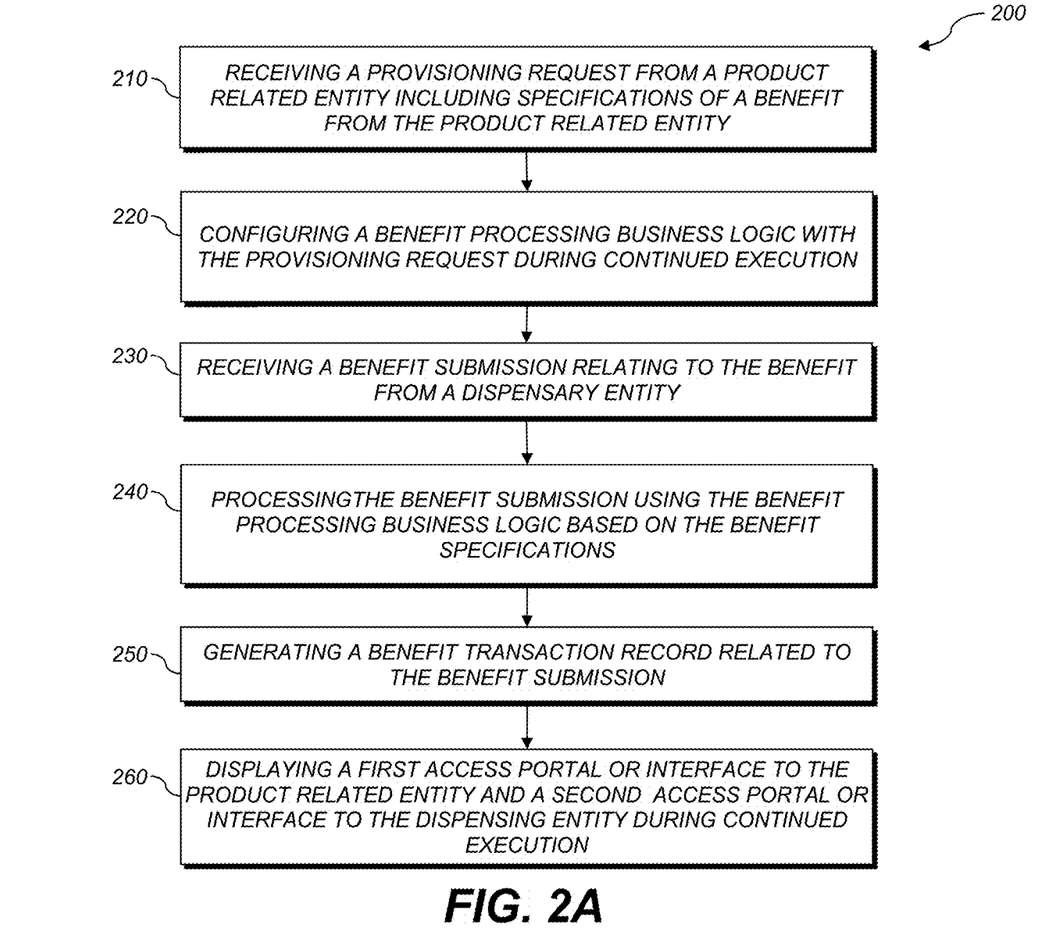
FIG. 2A is a flowchart depicting a benefit management method, in accordance with one or more aspects set forth herein.

FIG. 2A is a flowchart depicting a benefit management method 200. In one embodiment, the method 200 at block 210 receives a provisioning request from a first processor controlled by a product related entity. The provisioning request includes specifications of a product benefit offering from the product related entity.

In one example, the medical benefit management method may also receive one or more configuration requests from the product related entity or the dispensary entity, the configuration request comprising entity configuration information. In another example, a plurality of provisioning requests may be received from a plurality of product related entities, and may correspondingly include specifications of a plurality of product benefit offerings from the plurality of product related entities.

The method 200 at block 220 provisions a benefit processing business logic of the benefit processing system with the provisioning request. Provisioning the business logic occurs during continued operation of the benefit processing system. For example, provisioning the benefit processing business logic may include generating one or more business rules based on the provisioning request.

In one example, the medical benefit management method provisions the benefit processing business logic of the medical benefit management system with the plurality of provisioning requests. In such a case, the provisioning may also occur during continued operation of the medical benefit management system.

By way of explanation, the business logic may include rules that are triggered during the benefit processing specific to any of the business entities. The business rules can be updated in real-time by the benefit processing system to a specific entity without impacting the rules for any other entities. Examples of business logic are set forth in FIGS. 4 & 5.

The method 200 at block 230 receives a benefit submission from a second processor controlled by a dispensary entity. The benefit submission relating to the product benefit offering from the product related entity.

In one example, the benefit submission is received via a clearinghouse. Different benefit submissions from different dispensaries may be received from the same or from different clearinghouses. In another example, the method securely validates the benefit submission before processing the benefit submission. In a further example, the benefit submission is not received via the clearinghouse, but instead is received directly by the medical benefit management method and system. In another example, a plurality of benefit submissions is received from a plurality of dispensary entities, each relating to a plurality of product offerings from the plurality of product related entities, and when received, the method generates a plurality of benefit transaction records related to the plurality of benefit submissions. Different submission types include those that are received from a clearinghouse or those received directly from an authorized dispensary.

Figure 4:
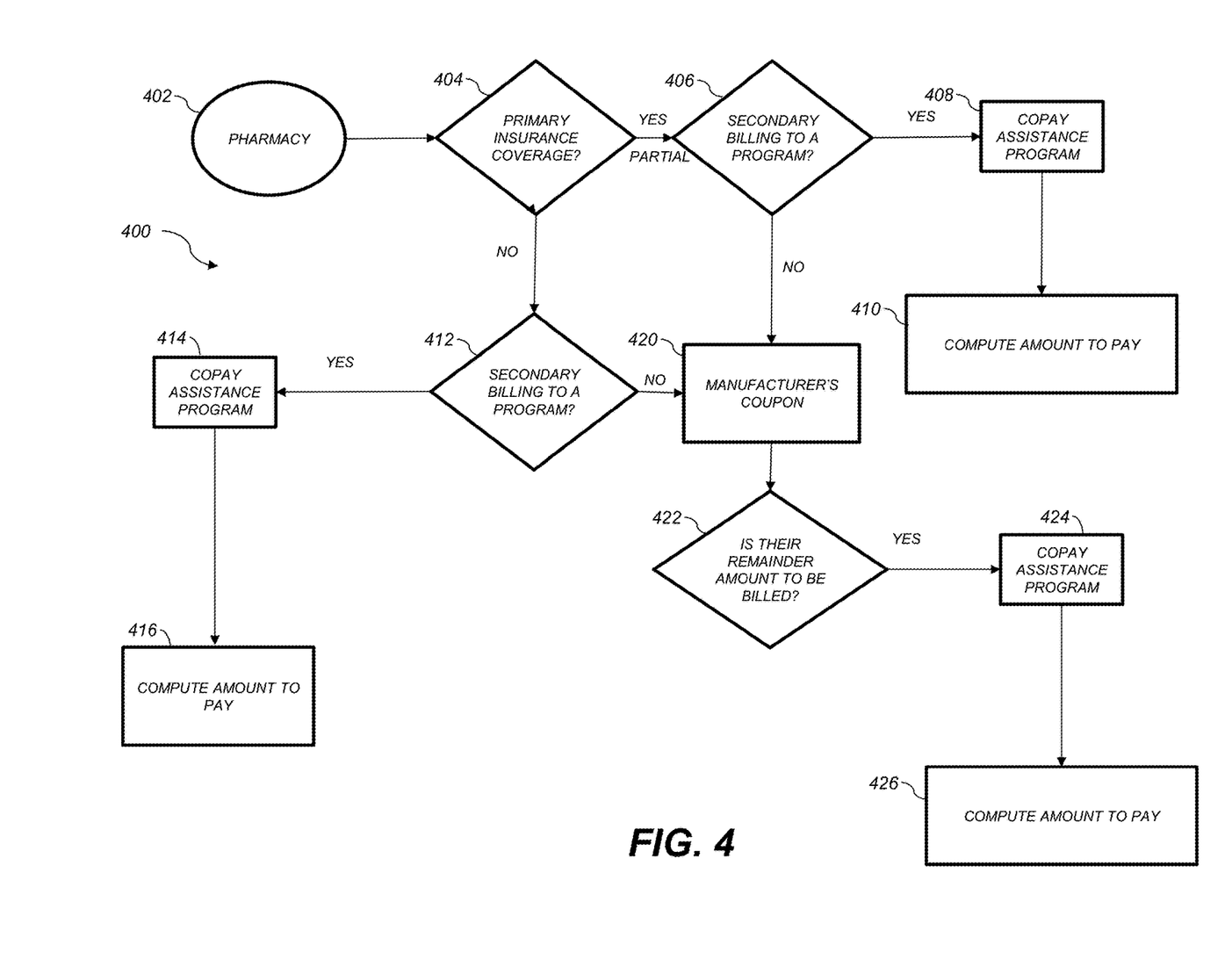
FIGS. 4-5 are flowcharts depicting business logic for execution by the medical benefit management system of FIG. 1A, in accordance with one or more aspects set forth herein.
Figure 5:
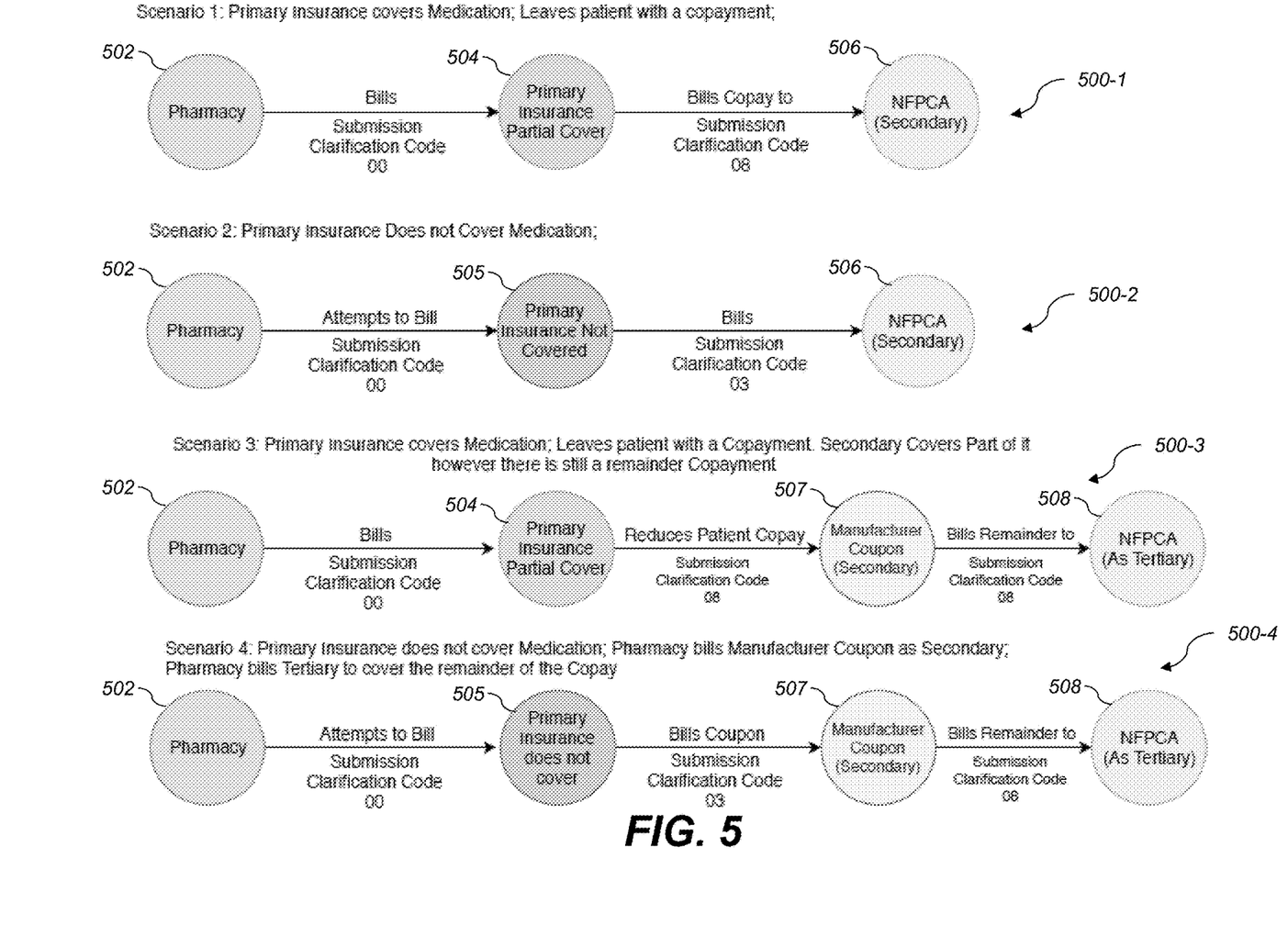

The method 200 at block 240 processes the benefit submission using the benefit processing business logic in view of the product offering. For instance, a rules engine executes algorithms for each entity and their corresponding benefit submission, as depicted in FIGS. 4-5.

Next, the method 200 at block 250 generates a benefit transaction record related to the benefit submission. In one example, the records received from dispensaries are rows of data that are processed during the transmission from the clearinghouse and are distributed into several segmented databases tables. The data is processed for efficiency and quick lookups that become available for each entity to view and consume their information.

At any time during the execution of any of the steps of the method 200, the method 200 at block 260 can display multiple interfaces for each entity. Each of the interfaces may comprise different views to different portions of the benefit transaction record related to the benefit submission. For example, each entity can be provisioned to view the data that is related to the entity itself. That data is trimmed based on access and can be viewed differently based on configured dashboard and different views of the interface.

In another example, the interface server can provide several different views for each of the different entities, to different portions of the plurality of benefit transaction records related to the plurality of benefit submissions.

Figure 2B:
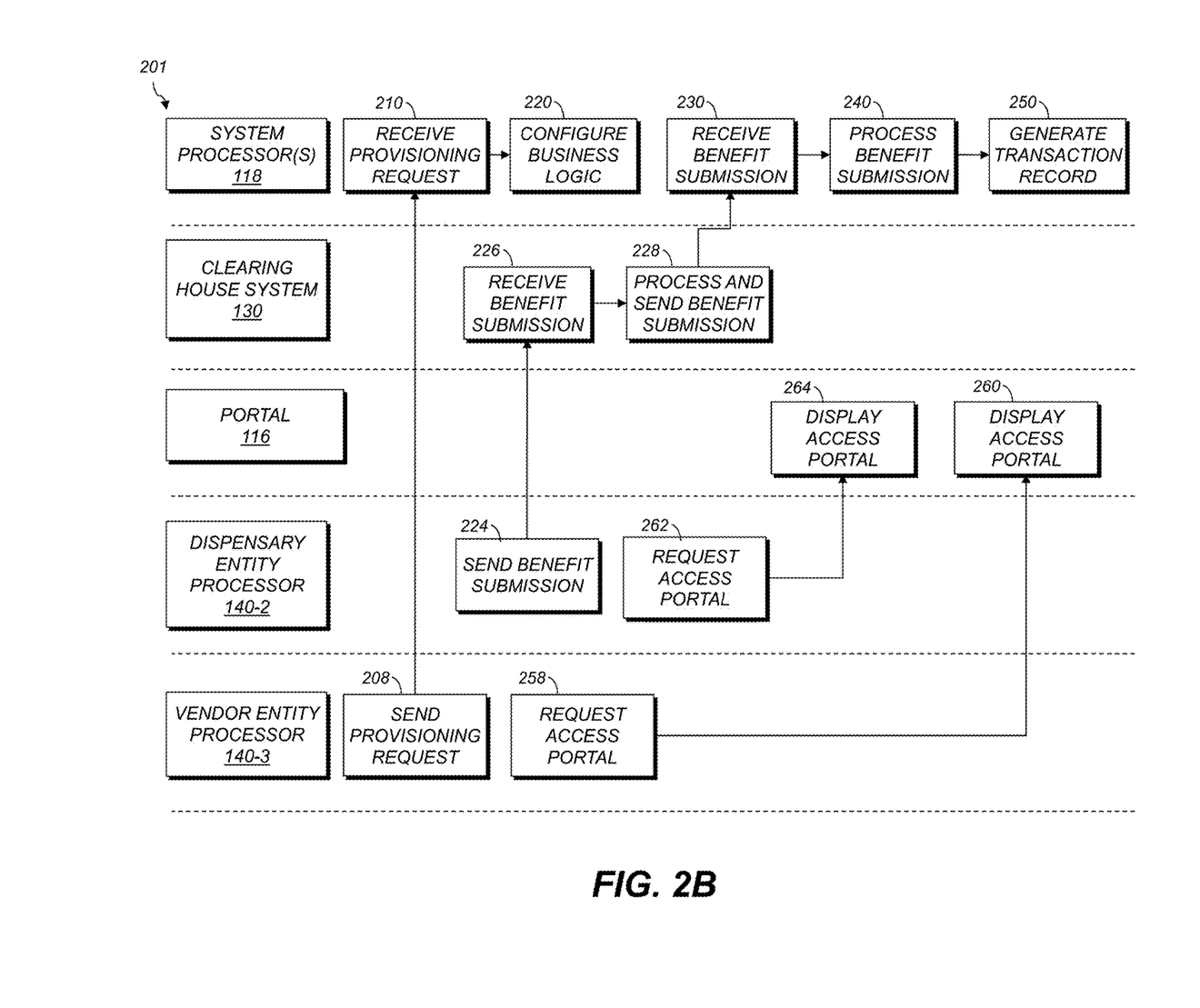
FIG. 2B is a flowchart depicting a benefit management method, in accordance with one or more aspects set forth herein.

FIG. 2B is a flowchart depicting a benefit management method 201. In the embodiment of FIG. 2B, the method 201 is performed by processor(s) 118 of the medical benefit management system 110 of FIG. 1A including the interface 116 thereof, the clearinghouse system 130, and two example entities. The two example entities for the embodiment of FIG. 2B include the dispensary entity processor 140-2 and the vendor entity processor 140-3. FIG. 2B shows 5 horizontal lanes with a component on the left and method steps performed by that component, in an embodiment, indicated its right in the same horizontal lanes. However, in different embodiments, the different steps of the method may be performed by other components, such as in a situation where multiple roles are performed by a single computer system.

Continuing now with FIG. 2B, the vendor entity processor 140-3 performs the step of the method 201 at block 208 to send a provisioning request to the system processor(s) 118. Next, the system processor(s) 118 performs the steps of the method 201 at block 210 to receive the provisioning request from the vendor entity processor 140-3. Next, the system processor(s) 118 performs the steps of the method 201 at block 220 to configure a benefit processing business logic of the benefit processing system 110 (FIG. 1A) with the provisioning request.

In one embodiment, the dispensary entity processor 140-2 performs the step of the method 201 at block 224 to send a benefit submission to the clearinghouse system 130. Then, the clearinghouse system 130 performs the steps of the method 201 at block 226 to receive the benefit submission from the dispensary entity processor 140-2. Next, the clearinghouse system 130 performs the steps of the method 201 at block 228 to process the benefit submission and send it to the appropriate entity, which in this case is the system processor(s) 118.

Continuing, the system processor(s) 118 performs the steps of the method 201 at block 230 to receive the benefit submission from the clearinghouse system 130 (which had ultimately received the benefit submission from the dispensary entity processor 140-2). Thereafter, the system processor(s) 118 performs the steps of the method 201 at block 240 to process the benefit submission using the benefit processing business logic in view of the product offering. This could be the benefit processing logic previously provisioned at block 220, which may have been invoked repeatedly to load numerous different business processing logic and rules for all the different benefit programs supported by the specific instance of a benefit management system 110.

Next, the system processor(s) 118 performs the steps of the method 201 at block 250 generates a benefit transaction record related to the benefit submission. The record is stored internally in a database as discussed above, and memorializes the benefit transaction.

A person of ordinary skill in the art would readily understand that the steps discussed in the paragraphs above would be repeated hundreds, thousands, or millions of times, in the normal processing of a variety of benefit claims for numerous patients. The repeated transaction records would then be available in the medical benefit management system for subsequent access and interrogation.

For instance, any of the entities can then access the information as follows. In one example, the vendor entity processor 140-3 performs the steps of the method 201 at block 258 to request access to a client specific interface. The interface 116 then performs the steps of the method 201 at block 260 to display only a interface that is specific to the vendor entity processor 140-3, based on the permissions used for logging into the interface. Similarly, the dispensary entity processor 140-2 may perform the steps of the method at block 262 to request access to an interface, and the interface 116, in turn, may perform the steps of the method 201 at block 264 to display a specific access interface for the dispensary entity processor 140-2. These interface views will be different for each entity, and provide different views into the same data.

Figure 3:
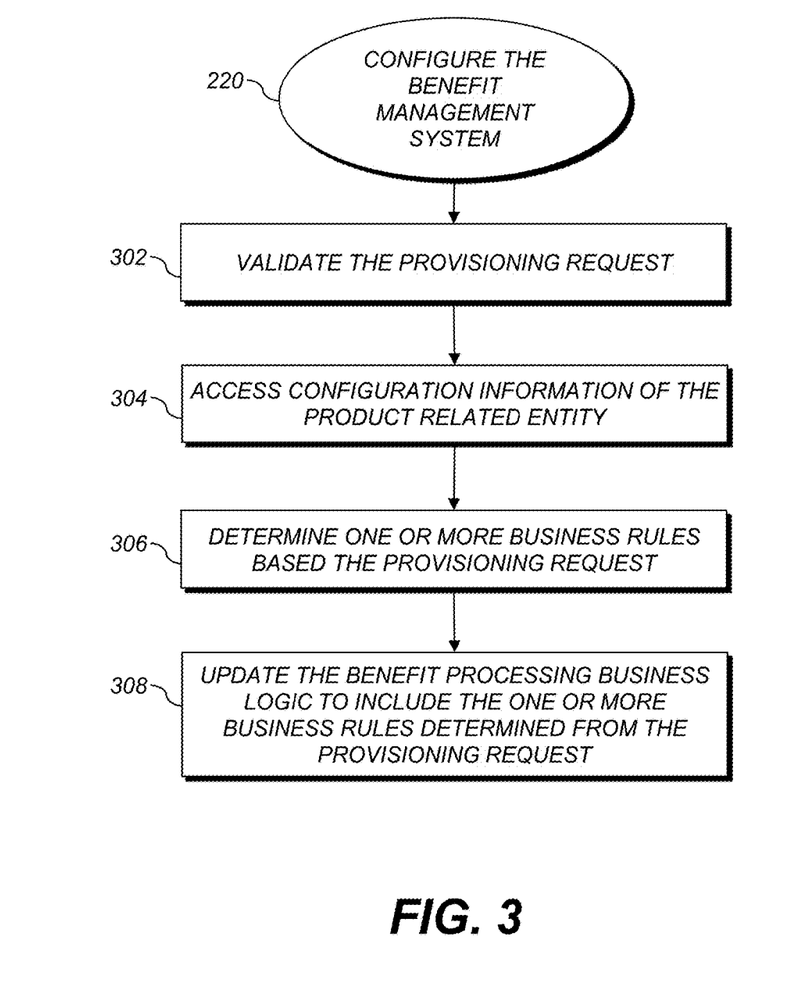
FIG. 3 is a flowchart depicting provisioning of a benefit management system, in accordance with one or more aspects set forth herein.

FIG. 3 is a flowchart depicting another embodiment of provisioning of a benefit management system 220. In the embodiment of FIG. 3, provisioning the medical benefit management system at block 220 includes at block 302 validating the provisioning request. Next, at block 304, the method accesses configuration information of the product related entity. For instance, each vendor or manufacturer may have been configured with different operating parameters, relating to which types of business logic are supported. Next, at block 306, the method determines the business rules to be loaded for the provisioning request, in light of the configuration for that entity. Then, at block 308, the method updates the business processing business logic to include these business rules that have been determined.

FIGS. 4-5 are flowcharts depicting business logic for execution by the medical benefit management system of FIG. 1A, in accordance with one or more aspects set forth herein. For example, the business logic examples of FIGS. 4-5 may be provisioned within the benefit processing system based on receiving a provisioning request from a product related entity. These examples in no way limit the scope of the present disclosure, and numerous other business logic examples may be supported by the system.

Turning to FIG. 4, depicted is a business logic 400 that includes numerous processing flows which may occur in different orders. Depending on the order in which the business logic 400 executes, different outcomes result.

In a first example, the business logic 400 may process a benefit submission by executing sequentially blocks 402, 404, 406, 408, and 410. In such a case, at block 402, a medical merchant (e.g., a pharmacy) begins a benefit submission transaction. At block 404, primary insurance coverage is determined. If full or partial coverage is determined, at block 406 secondary billing to a program is determined. If yes, at block 408 a copy assistance program is accessed. Then, at block 410, an amount to pay by the copay assistance program is computed. The business logic 400 then generates a benefit transaction record related to the benefit submission of this example.

In a second example, the business logic 400 may process a benefit submission by executing sequentially blocks 402, 404, 412, 414, and 416. In such a case, at block 402, a medical merchant (e.g., a pharmacy) begins a benefit submission transaction. At block 404, primary insurance coverage is determined. If no coverage is determined, at block 412 secondary billing to a program is determined. If yes, at block 414 a copy assistance program is accessed. Then, at block 416, an amount to pay by the copay assistance program is computed. The business logic 400 then generates a benefit transaction record related to the benefit submission of this example.

In a third example, the business logic 400 may process a benefit submission by executing sequentially blocks 402, 404, 406, 420, 422, 424, and 426. In such a case, at block 402, a medical merchant (e.g., a pharmacy) begins a benefit submission transaction. At block 404, primary insurance coverage is determined. If full or partial coverage is determined, at block 406 secondary billing to a program is determined. If not, at block 420, a manufacturer's coupon is accessed. At block 422, a determination is made of whether there is still a remaining amount to be billed. If yes, at block 424 a copy assistance program is accessed. Then, at block 426, an amount to pay by the copay assistance program is computed. The business logic 400 then generates a benefit transaction record related to the benefit submission of this example.

In a fourth example, the business logic 400 may process a benefit submission by executing sequentially blocks 402, 404, 412, 420, 422, 424 and 426. In such a case, at block 402, a medical merchant (e.g., a pharmacy) begins a benefit submission transaction. At block 404, primary insurance coverage is determined. If no coverage is determined, at block 412 secondary billing to a program is determined. If not, at block 420, a manufacturer's coupon is accessed. At block 422, a determination is made of whether there is still a remaining amount to be billed. If yes, at block 424 a copy assistance program is accessed. Then, at block 426, an amount to pay by the copay assistance program is computed. The business logic 400 then generates a benefit transaction record related to the benefit submission of this example.

FIG. 5 depicts yet other examples of business logic 500-1, 500-2, 500-3 and 500-4. A first example handles a scenario in which primary insurance covers medication but leaves a patient with a co-payment. In such a case, business logic 500-1 at block 502 receives a benefit submission transaction including a claim for payment of a prescription. Then, at block 504 primary insurance partially covers the claim. Next, at block 506, a copay assistance program (one example of which is the National Foundation for Prescription Copay Assistance, or NFPCA) processes and pays as a secondary.

A second example handles a scenario in which primary insurance does not cover medication. In such a case, business logic 500-2 at block 502 receives a benefit submission transaction including a claim for payment of a prescription. Then, at block 505 primary insurance does not cover the claim. Next, at block 506, a copay assistance program (one example of which is the National Foundation for Prescription Copay Assistance, or NFPCA) processes and pays as a secondary.

A third example handles a scenario in which primary insurance covers medication and leaves a patient with a copayment, and secondary covers part of the cost, leaving a remainder copayment. In such a case, business logic 500-1 at block 502 receives a benefit submission transaction including a claim for payment of a prescription. Then, at block 504 primary insurance partially covers the claim. Next, at block 507, a manufacturer coupon is available to cover as a secondary. Next, at block 508, a copay assistance program (one example of which is the National Foundation for Prescription Copay Assistance, or NFPCA) processes and pays as a tertiary.

A fourth example handles a scenario in which primary insurance does not cover medication, the medical merchant (e.g., the pharmacy) bills a manufacturer coupon as a secondary, and the medical merchant bills a tertiary program to cover the remainder of the copay. In such a case, business logic 500-2 at block 502 receives a benefit submission transaction including a claim for payment of a prescription. Then, at block 505 primary insurance does not cover the claim. Next, at block 507, a manufacturer coupon is available to cover as a secondary. Next, at block 508, a copay assistance program (one example of which is the National Foundation for Prescription Copay Assistance, or NFPCA) processes and pays as a tertiary.

The example business logic described above may be encoded in configuration files and loaded by the different product related entities as new programs are added and changed.

Figure 6:
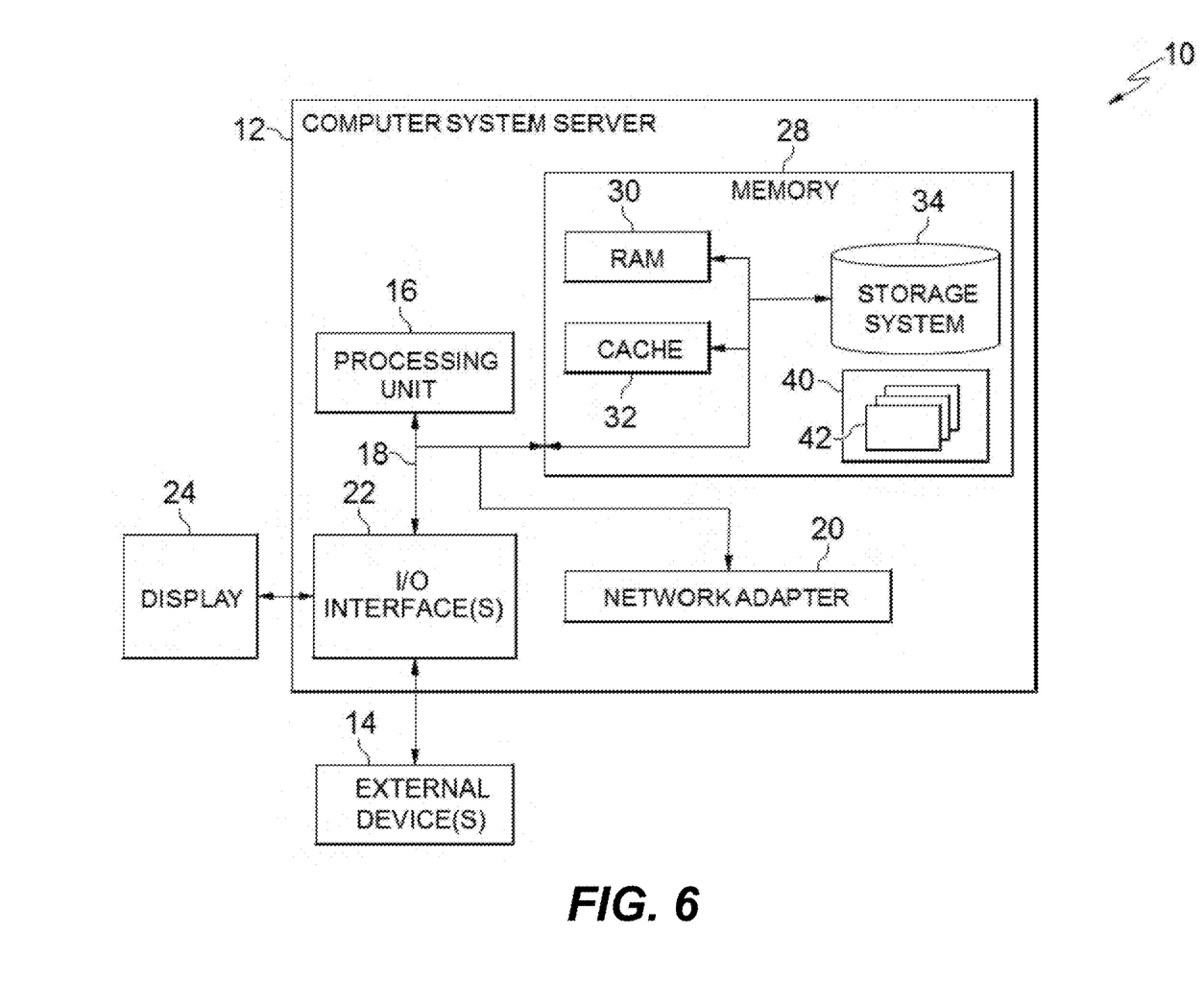
FIG. 6 is a block diagram of a computer system, such as that employed by the medical benefit management system of FIG. 1A.

FIG. 6 is a block diagram of a computer system 10, such as that employed by the medical benefit management system 110 of FIG. 1A. A computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed environments where tasks are performed by remote processing devices that are linked through a communications network. In a distributed environment, program modules may be located in both local and remote computer system storage media including memory storage devices.

Computer system/server 12 in computer system 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Embodiments may include a system, a method, and/or a computer program product. The computer program product may include a computer readable storage medium (or media) having computer readable program instructions thereon for causing a processor to carry out aspects of set forth herein.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the certain embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects set forth herein.

Embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system for configuration, management and payment of medical benefits related to a plurality of medical merchants, the system enabling rule customization in real-time using a plurality of configuration files for encoding business logic without impacting continued operation of benefit processing, the system comprising:
 a provider server system;
 a merchant server system; and
 a medical benefit management system comprising
  a connection manager for receiving the plurality of configuration files for encoding business logic,
  a stream processor for managing communications with the provider server system and the merchant server system, a portal server, and one or more data storage devices comprising a plurality of computer-readable instructions, wherein the instructions comprise a plurality of benefit business rules, wherein the instructions are executable by one or more processors to cause the one or more processors to:

receive using the connection manager a first configuration file from the provider server system comprising offering data from a provider, wherein the offering data specifies at least one medical benefit offering that is associated with a product marketed by the provider;

receive using the connection manager a second configuration file from the provider server system comprising at least one rule customization input from the provider;

customize, in real-time without impacting continued operation of the system, at least one of the benefit business rules based, at least in part, on the at least one rule customization input, wherein the at least one rule customization input comprises processing logic to determine a primary payer, a secondary payer and a tertiary payer of an insurance benefit, wherein the system concurrently operate to receive and process benefit submissions during the customizing;

receive using the connection manager a third file from the merchant server system comprising a benefit submission from a medical merchant, wherein the benefit submission is based, at least in part, on a medical request received by the medical merchant, wherein the medical request is provided by a customer;

process the benefit submission using the at least one customized business rule, wherein the processing comprises executing the processing logic based on the received benefit submission to determine payment by the primary payer, the secondary payer and the tertiary payer;

generate benefit transaction information related to the benefit submission, wherein the benefit transaction information comprises a first portion and a second portion that differs from the first portion; and cause a plurality of display devices to simultaneously display a provider interface accessible by the provider using the portal server and a merchant interface accessible by the medical merchant using the portal server, wherein:

the provider interface displays the first portion and blocks access to the second portion; and the merchant interface displays the second portion and blocks access to the first portion, such that the portal server displays different views of the benefit transaction information to the provider and the medical merchant; and generate a benefit outcome based on the processing of the benefit submission, wherein the benefit outcome results in the at least one medical benefit being provided by the medical merchant to the customer.

2. The medical benefit management system of claim 1, wherein the benefit outcome comprises a copay reduction for the customer.

3. A medical benefit management system for enabling rule customization in real-time using a plurality of provisioning requests for encoding business logic without impacting continued operation of benefit processing, the system comprising:

a portal server; and one or more data storage devices storing a plurality of instructions, the plurality of instructions comprising a benefit processing business logic, and the plurality of instructions configured to be executed to:

receive a provisioning request from a first processor controlled by a product related entity, the provisioning request comprising a benefit specification from the product related entity, wherein the benefit specification comprises the benefit processing business logic to determine a primary payer, a secondary payer and a tertiary payer of an insurance benefit, wherein the system continues to operate to receive and process benefit submissions during the customizing;

configuring, in real-time without impacting continued operation of the system, the benefit processing business logic with the provisioning request, the provisioning occurring during execution of the plurality of instructions;

receive a benefit submission from a second processor controlled by a dispensary entity, the benefit submission relating to the benefit specification from the product related entity;

process the benefit submission using the configured benefit processing business logic, wherein the processing comprises executing the benefit processing business logic based on the received benefit submission to determine payment by the primary payer, the secondary payer and the tertiary payer;

generate a benefit transaction record related to the benefit submission; and display a first access interface to the product related entity and a second access interface to the dispensing entity using the portal server, wherein the first and second access interfaces are accessible via the portal server during continued operation and comprise different views to different portions of the benefit transaction record related to the benefit submission.

4. The medical benefit management system of claim 3, wherein the benefit processing business logic comprises one or more business rules based on the provisioning request.

5. The medical benefit management system of claim 3, wherein the product related entity comprises a manufacturer of a product related to the benefit specification.

6. The medical benefit management system of claim 3, wherein the benefit submission is received via a clearinghouse.

7. The medical benefit management system of claim 6, wherein the benefit submission is not received via the clearinghouse.

8. The medical benefit management system of claim 3, wherein the plurality of instructions are further configured to be executed to receive a plurality of provisioning requests from a plurality of product related entities, the plurality of provisioning requests comprising specifications of a plurality of benefit specifications from the plurality of product related entities.

9. The medical benefit management system of claim 8, wherein the plurality of instructions are further configured to be executed to provision the benefit processing business logic of the medical benefit management system with the plurality of provisioning requests, the provisioning occurring during continued operation of the benefit management system.

10. The medical benefit management system of claim 9, wherein the plurality of instructions are further configured to receive a plurality of benefit submissions from a plurality of dispensary entities, the plurality of benefit submissions relating to the plurality of benefit specifications from the plurality of product related entities, and generate a plurality of benefit transaction records related to the plurality of benefit submissions.

11. The medical benefit management system of claim 10, wherein the plurality of instructions are further configured to provide a plurality of first interfaces to the plurality of product related entities and a plurality of second interfaces to the plurality of dispensary entities, wherein the first and second pluralities of interfaces are accessible during continued operation of the benefit management system and comprise different views to different portions of the plurality of benefit transaction records related to the plurality of benefit submissions.

12. The medical benefit management system of claim 3, wherein the plurality of instructions are further configured to securely validate the benefit submission before processing the benefit submission.

13. The medical benefit management system of claim 3, wherein the benefit submission is related to multiple products.

14. The medical benefit management system of claim 3, wherein the plurality of instructions is further configured to be executed to receive one or more configuration requests from the product related entity or the dispensary entity, the configuration request comprising entity configuration information.

* * * * *